(12) United States Patent
Takeda

(10) Patent No.: US 11,455,440 B2
(45) Date of Patent: Sep. 27, 2022

(54) GRAPHIC USER INTERFACE ASSISTED CHEMICAL STRUCTURE GENERATION

(71) Applicant: INTERNATIONAL BUSINESS MACHINES CORPORATION, Armonk, NY (US)

(72) Inventor: Seiji Takeda, Tokyo (JP)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 886 days.

(21) Appl. No.: 16/284,011

(22) Filed: Feb. 25, 2019

(65) Prior Publication Data

US 2020/0272702 A1    Aug. 27, 2020

(51) Int. Cl.
*G06F 30/20* (2020.01)
*G16C 20/80* (2019.01)
*G06N 3/04* (2006.01)

(52) U.S. Cl.
CPC ........... *G06F 30/20* (2020.01); *G06N 3/0454* (2013.01); *G16C 20/80* (2019.02)

(58) Field of Classification Search
CPC ......... G06F 30/20; G06F 30/25; G06F 30/27; G06F 30/28; G06F 2111/00; G06F 2119/22; G06N 3/0454; G06N 3/0472; G16C 20/80
See application file for complete search history.

(56) References Cited

U.S. PATENT DOCUMENTS

2017/0193200 A1* 7/2017 Hsu .................. G16C 20/30
2017/0344674 A1  11/2017 McCloskey et al.

FOREIGN PATENT DOCUMENTS

| CN | 107480429 A | 12/2017 |
| JP | 2018092575 A | 6/2018 |
| WO | 2014087427 A1 | 6/2014 |

OTHER PUBLICATIONS

Michael Reutlinger, et al., "Nonlinear dimensionality reduction and mapping of compound libraries for drug discovery," Journal of Molecular Graphics and Modelling 34 pp. 108-117 (Year: 2012).*
David Koes, et al., "Enabling Large-Scale Design, Synthesis and Validation of Small Molecule Protein-Protein Antagonists," PLoS ONE vol. 7 p. 1-8 (Year: 2012).*

(Continued)

*Primary Examiner* — Steven W Crabb
(74) *Attorney, Agent, or Firm* — Tutunjian & Bitetto, P.C.; Randall Bluestone

(57) ABSTRACT

A computer implemented method of generating new chemical compounds is provided. The method includes preparing a feature vector for each of a plurality of chemical compounds for which a chemical or physical property is known. The method further includes compressing each of the feature vectors into a relational vector, and mapping each of the relational vectors to a map having at least two dimensions. The method further includes presenting the map on a display device. The method further includes receiving a selection of a position on the map, wherein the position is converted to a new relational vector, and decompressing the new relational vector to a candidate feature vector. The method further includes generating a new chemical structure from the candidate feature vector.

18 Claims, 10 Drawing Sheets

(56) References Cited

OTHER PUBLICATIONS

Connor W. Coley, et al., "A graph-convolutional neural network model for the prediction of chemical reactivity," Chem. Sci 2019 (Year: 2019).*
"Polymer Genome: An Informatics Platform for Accurate Property Estimates of Existing and Hypothetical Polymers Using Machine Learning MOdels Trained on a Benchmark Dataset", https://www.polymergenome.org/explore/index.php?m=1, Aug. 2018, 2 pages.
"MOLGEN Molecular Structure Generation", http://www.molgen.de/, Oct. 2018, 2 pages.
"DeepChem is a Phyton Library Democratizing Deep Learning for Science", https://github.com/deepchem/deepchem, Jan. 2019, 5 pages.

* cited by examiner

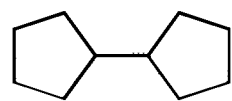
(A)
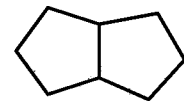
(B)
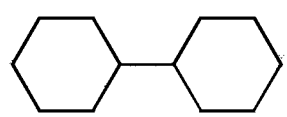
(C)
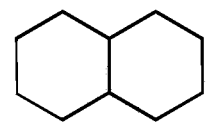
(D)
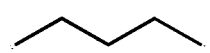
(E)
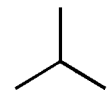
(F)
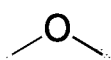
(G)
(H)
FIG. 6

FIG. 7 ORIGINAL

GRAPHIC USER INTERFACE ASSISTED CHEMICAL STRUCTURE GENERATION

BACKGROUND

Technical Field

The present invention generally relates to graphical user interfaces (GUI), and more particularly to GUI-assisted chemical structure generation.

Description of the Related Art

Identifying and designing new chemical structures that have particular intended properties for synthesis can be very time consuming and expensive. Researchers can spend extensive amounts of time and effort attempting to discover new chemical compounds having a desired set of properties, but much trial and error can be involved in such research efforts. In addition, researchers can be limited by the scope of their past learning and experiences, such that the direction of their research efforts can include biases and be limited by incomplete knowledge of the huge amount of data available for known chemical structures and their properties. Use of their intuition in coming up with hopeful new chemical candidates for synthesis and testing can lead researchers down unfruitful paths before sufficient familiarity and understanding of the structure/property relationships may be acquired.

SUMMARY

In accordance with an embodiment of the present invention, a computer implemented method of generating new chemical compounds is provided. The method includes preparing a feature vector for each of a plurality of chemical compounds for which a chemical or physical property is known. The method further includes compressing each of the feature vectors into a relational vector, and mapping each of the relational vectors to a map having at least two dimensions. The method further includes presenting the map on a display device. The method further includes receiving a selection of a position on the map, wherein the position is converted to a new relational vector, and decompressing the new relational vector to a candidate feature vector. The method further includes generating a new chemical structure from the candidate feature vector.

In accordance with another embodiment of the present invention, a system for generating new chemical compounds is provided. The system includes a display device, memory, wherein a data set of a plurality of chemical compounds for which a chemical or physical property is stored in the memory, and a processor device, wherein the processor device is configured to prepare a feature vector for each of a plurality of chemical compounds for which a chemical or physical property is known. The system further includes a chemical structure generator configured to compress each of the feature vectors into a relational vector, map each of the relational vectors to a map having at least two dimensions, present the map on the display device, receive a selection of a position on the map, wherein the position is converted to a new relational vector, decompress the new relational vector to a candidate feature vector, and generate a new chemical structure from the candidate feature vector.

In accordance with yet another embodiment of the present invention, a non-transitory computer readable storage medium comprising a computer readable program for generating new chemical compounds is provided. The computer readable program when executed on a computer causes the computer to perform the steps of: preparing a feature vector for each of a plurality of chemical compounds for which a chemical or physical property is known, compressing each of the feature vectors into a relational vector, mapping each of the relational vectors to a map having at least two dimensions, presenting the map on a display device, receiving a selection of a position on the map, wherein the position is converted to a new relational vector, decompressing the new relational vector to a candidate feature vector, and generating a new chemical structure from the candidate feature vector.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 6 is a diagram showing a set of predefined features used to form a predefined component feature vector, in accordance with an embodiment of the present invention;

DETAILED DESCRIPTION

Figure 1:
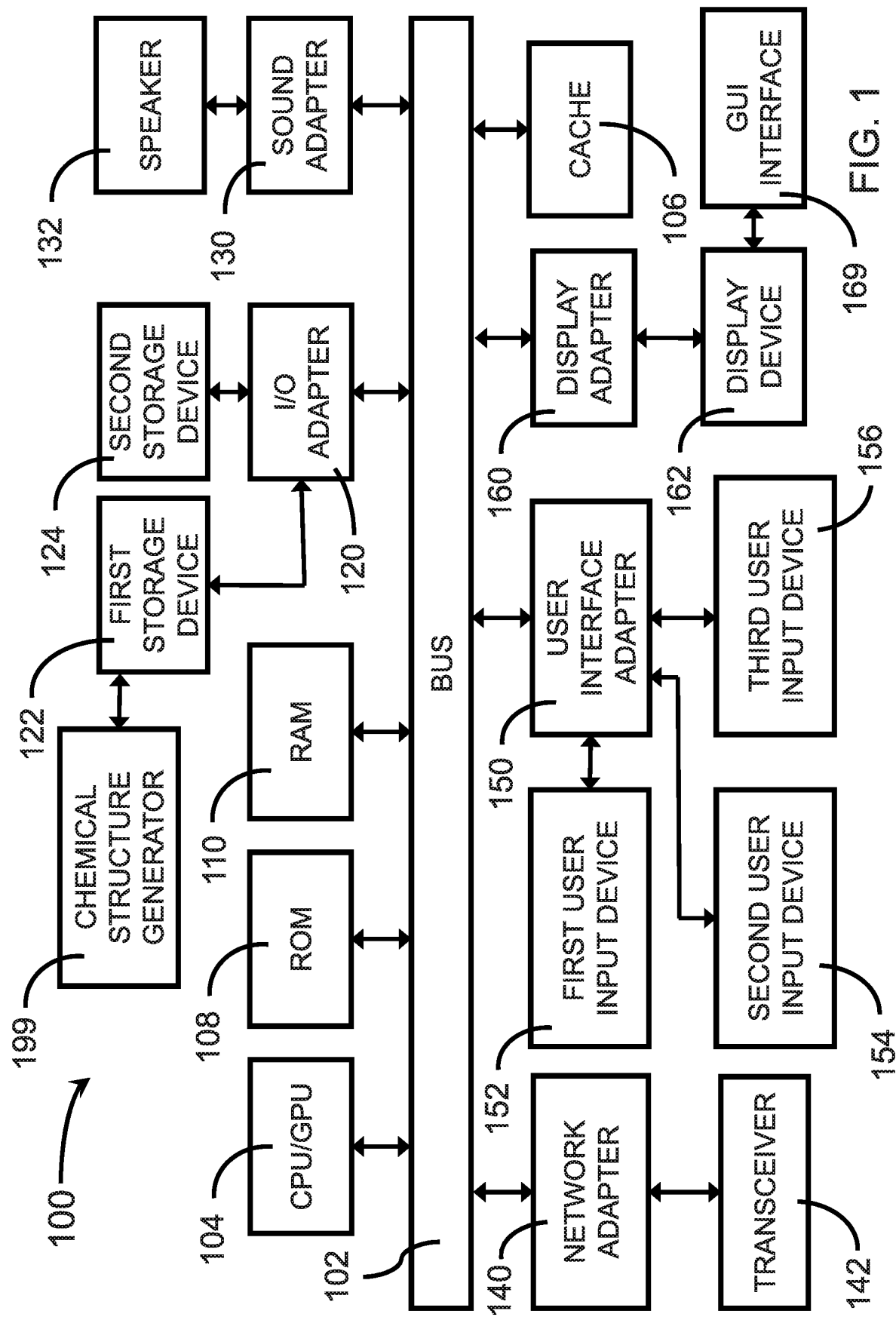
FIG. 1 is a diagram showing an exemplary processing system, in accordance with an embodiment of the present invention.

Embodiments of the present invention relate generally to the creation of new chemical compounds having desired properties using accumulated chemical data to construct a new chemical structure for synthesis. The desired properties can be identified by users using a graphical user interface (GUI) that displays a dimension reduced feature space related to the desired properties. Large amounts of data on known chemical compounds can be digested and utilized to generate and present a 2-dimensional map of chemical compounds having desired chemical and/or physical properties through a relational vector. New chemical structures can be generated by selecting a position on the 2-dimensional map that were not previously available to produce a new relational vector to generate a new chemical structure, thereby reducing or eliminating the expense of the trial and error approach or use of common sense by human researchers.

Embodiments of the present invention relate generally to automating material discovery by utilizing the known structures of chemical compounds with correlated physical and chemical properties to identify and design new materials with particular chemical structures that can provide specific intended physical and/or chemical properties. The identification of the new materials can be based upon a relative position between the known chemical structure and associated properties and a selected position on a 2-dimensional map. Feature vectors for known chemical compounds can be automatically generated by manipulating character strings representing each molecular structure, and the new chemical structure can be generated through the special relationship on the 2-dimensional map representing the feature vectors utilizing a dimension-reduced feature space.

Embodiments of the present invention relate generally to a GUI-assisted chemical structure generator with a dimension-reduced feature space displayed to a user as a 2-dimensional map. A user can identify a property relationship in the dimension-reduced feature space by identifying a position on the 2-dimensional map in a GUI interface that maps to a new chemical structure based on the relationship of relational vectors with known feature vectors. A new chemical structure having a particular chemical property can be designed by decompressing the position on the 2-dimensional map into a new feature vector representing components of a chemical structure from a feature table that identifies the substructures (e.g., backbone, chemical moieties, heteroatoms, etc.).

Embodiments of the present invention relate generally to a system for specifying the value of one or more desired chemical and/or physical properties that is not provided by the available set of chemical structures utilizing a GUI-assisted chemical structure generator, and generating a new chemical structure having the specified values of the one or more desired chemical and/or physical properties using data-driven feature vectors. In various embodiments, the system allows a user to intuitively and rapidly design new molecular structures with structural similarities and/or differences to one or more other known molecules, where the new molecular structure has a desired property.

Exemplary applications/uses to which the present invention can be applied include, but are not limited to: pharmaceutical drug discovery, biological drug discovery, materials synthesis, polymer synthesis, and inorganic compound synthesis.

Referring now to the drawings in which like numerals represent the same or similar elements and initially to FIG. 1, an exemplary processing system is shown, in accordance with an embodiment of the present invention.

An exemplary processing system 100 to which the present invention may be applied is shown in accordance with an embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, can be operatively coupled to the system bus 102.

A first storage device 122 and a second storage device 124 can be operatively coupled to system bus 102 by the I/O adapter 120. The storage devices 122 and 124 can be any of a disk storage device (e.g., a magnetic or optical disk storage device), a solid state device, a magnetic device, and so forth. The storage devices 122 and 124 can be the same type of storage device or different types of storage devices. A chemical structure generator 199 can be loaded into and/or stored in the first storage device 122 or second storage device 124 for execution by the processor device 104, including a graphics processing unit (GPU).

A speaker 132 can be operatively coupled to system bus 102 by the sound adapter 130. A transceiver 142 can be operatively coupled to system bus 102 by network adapter 140. A display device 162 can be operatively coupled to system bus 102 by a display adapter 160. A graphical user interface (GUI) 169 for the chemical structure generator 199 can be displayed on the display device 162, where the display device 162 can present a 2 dimensional map of relational vectors to a user.

A first user input device 152, a second user input device 154, and a third user input device 156 can be operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, for example, a graphic processor unit (GPU), controllers, memories, and so forth, in various configurations can also be utilized as readily appreciated by one of ordinary skill in the art. These and other variations of the processing system 100 are contemplated.

The processing system can be configured to implement a GUI-assisted chemical structure generator configured to compress each of the feature vectors into a 2×1 dimensional relational vector, map each of the 2×1 dimensional relational vectors to a 2 dimensional map, present the 2 dimensional map on the display device, receive a selection of a position on the 2 dimensional map, wherein the position is converted to a new 2×1 dimensional relational vector, decompress the new 2×1 dimensional relational vector to a candidate feature vector, and generate a new chemical structure from the candidate feature vector using a processor device.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
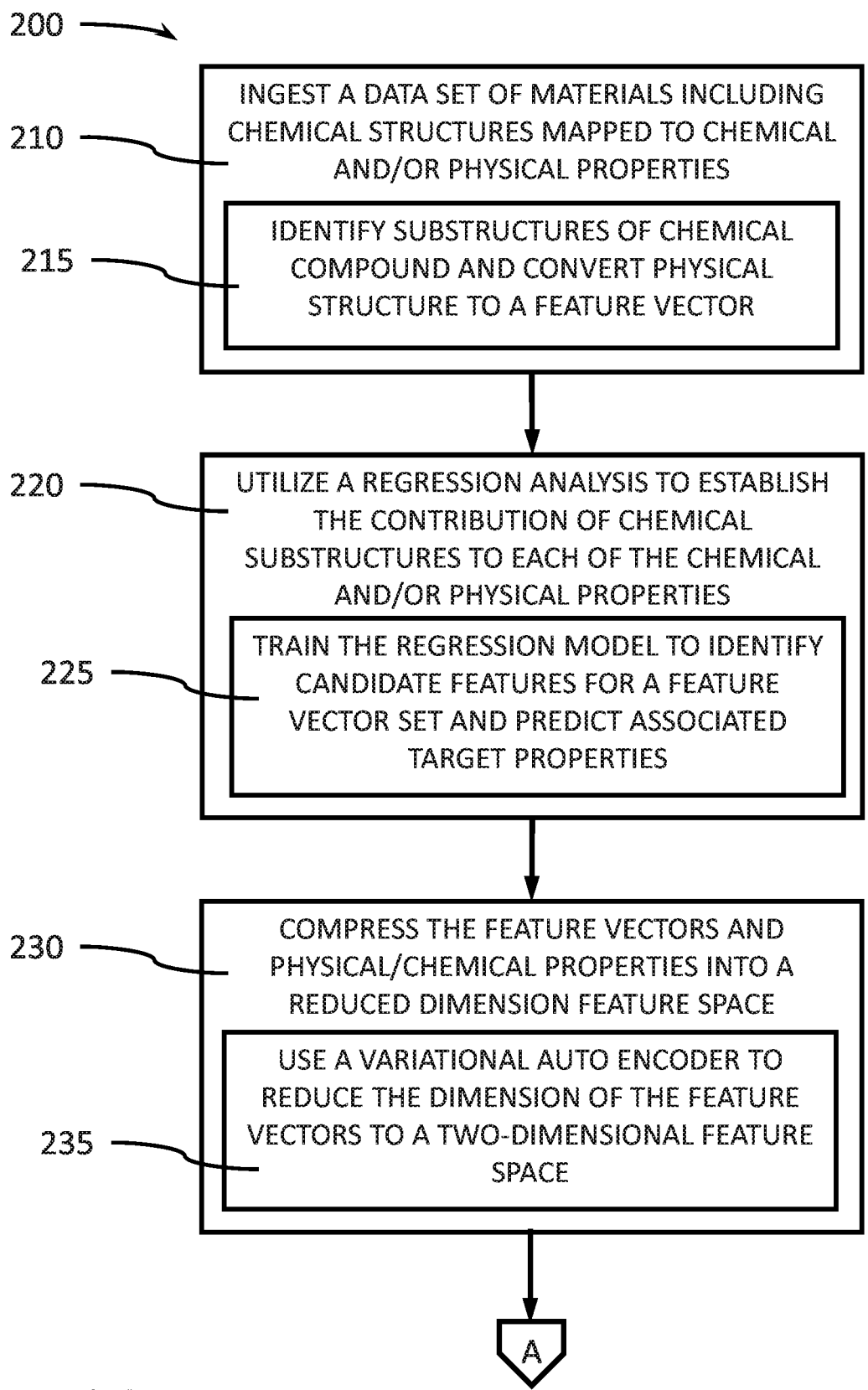
FIG. 2 is a block/flow diagram showing a general algorithm for transforming a material data set consisting of chemical structures with associated properties to a map for identifying a new material, in accordance with an embodiment of the present invention.

FIG. 2 is a block/flow diagram showing a general algorithm for transforming a material data set consisting of chemical structures with associated properties to a new material, in accordance with an embodiment of the present invention.

Most chemical properties are affected by substructures included in the chemical structure of a compound (e.g., organic molecules, biological compounds, inorganic compounds, polymers, etc.). Regression analysis and modeling can be used to identify the contribution of separate substructure(s) in a compound to a specific property through analysis of a large data set of chemical compounds including the particular substructure(s). The converting of the chemical structures to feature vectors, regression analysis and modeling, and filtering of new candidate structures can be driven by data and automated analysis rather than human experience, as shown in the computer implemented process algorithm 200.

In block 210, a data set of materials including a plurality of chemical structures and chemical and/or physical properties associated with each of the chemical structures can be stored in computer memory, for example, in a database in memory (e.g., magnetic hard drive, solid-state memory, etc.) and/or on storage discs (e.g., optical, magnetic). The data set of materials can be accessed by a processing system 100 for automated analysis. The data set of materials can be in a digital format accessible by a processing system.

In one or more embodiments, a feature vector can be created for each chemical compound in the data set of materials by counting the number of each of all the possible specific substructure permutations identified in the chemical compound structure. Two different types of feature vectors can be created. The first type of feature vector can include a data-driven substructure count, and the second type of feature vector can include a predefined component count. Each feature vector can include values for the quantity of each identified substructure for a single chemical compound. The identity of each of all the possible specific substructure permutations for a single chemical compound can form a data-driven substructure set. In various embodiments, both feature vector types are used, where concatenation of the data-driven and the predefined feature vector sets are used. For example, feature vector $x=(x_{DD}, x_{PD})$, where DD is the data driven set and PD is the pre-defined set. A feature vector can be generated for each chemical structure, where the chemical structures can have known related chemical and/or physical properties.

In block 215, the data-driven substructure feature vector can be created by identifying the substructures of each chemical compound in the data set. Creation of the data-driven substructure feature vector can include identifying all of the possible ways a chemical structure can be subdivided with the atoms of the chemical compound represented as nodes and bonds represented as edges of a graph. The identified substructures can be recorded using simplified molecular-input line-entry system (SMILES). SMILES is a string obtained by printing the symbols for the nodes encountered in a depth-first tree traversal of the chemical graph. The chemical graph can first be trimmed to remove hydrogen atoms and cyclic components (cycles) broken to turn it into a spanning tree. Where cycles have been broken, numeric suffix labels are included to indicate the connected nodes. Parentheses are used to indicate points of branching on the tree. Other chemical table file formats can also be used, for example, MDL Molfile and structure-data file (SDL). The data-driven substructure feature vector can be automatically created from the chemical data set using a processing system 100.

The data-driven feature is powerful for modeling the relationship between molecular structure and associated property, but a full structure cannot be decoded by using this approach alone because some substructures may be independent, but some substructures may be partially overlapping. The data-driven features can be utilized as a structural filter for structures generated using pre-defined features.

Counts of substructures do not provide information about their connections (e.g., bond type) nor the extent of their overlapping (e.g., sharing of the same nodes and/or edges), therefore a molecule cannot be built from the individual substructures. Information about building components of a molecule from which a molecular structure can be directly generated can be introduced using the feature vector of pre-defined components and counts. A data-driven substructure feature set and a pre-defined component feature set can collaborate to generate structures, and the data-driven features can work as a structural filter for structures generated by the pre-defined features.

A predefined component count for the second type of feature vector can be created from predefined building blocks intended to be analyzed and used to generate the new chemical compound. Predefined substructures can provide information about three types of components: backbone, atoms, and bonds. The predefined building blocks can be substructures, including, but not limited to, heteroatoms (e.g., nitrogen (N), oxygen (O), sulfur (S), halogens (e.g., fluorine (F), chlorine (Cl), bromine (Br), etc.), etc.), aromatic rings (e.g., benzene, naphthalene, etc.), aliphatic rings (e.g., cyclopentane, cyclohexane, etc.), functional groups, (e.g., carbonyl (C=O), carboxylic acid (—COOH), alcohols (—OH), amines (—$NH_2$), amides (—CONH—), thiols (—$SH_2$), double bonds, triple bonds, the total number of atoms and/or each type of atom, backbone length/structure, etc. The predefined component feature vector can be created by identifying a quantity for each of the predefined building blocks. The identity of each of the predefined components can form a predefined component set. In various embodiments, the feature vector can be, for example, a 66×1 dimension vector.

In block 220, a regression model can be created to correlate the known chemical structures and substructures to the known chemical and/or physical properties of the chemical compounds. The regression model can be used to predict associated chemical and/or physical properties from the substructures, where the extent that a substructure influences a property can be determined.

A regression model, F, can be built to predict a target property, y, from an identified set of substructures, where $F: \mapsto y$, where x is a concatenated feature vector $x := (X_D^{Select}, x_P)$, and y is the property. The type of regression model, F, utilized can depend on both the type of material(s) identified and the target properties selected. A regression model can be independently created for each property as $F_1:x_1 \mapsto y_1$, $F_2:x_2 \mapsto y_2$, etc. The regression analysis may utilize any regression method to provide adequate accuracy, for example, a kernel ridge regression method, where the type of regression method selected may affect the total final accuracy of the predicted resulting value. In case that multiple chemical and/or physical properties are targeted, x, is a sum-set of $x^{(j)}$ for property $y_j$ given as $x = x^{(j)} \cup_{j=1}^{N} x^{(j)}$, where j is an index from 1 to the number, N, of properties selected, and $x^{(j)}$ for is the $j^{th}$ substructure that can contribute to the $j^{th}$ property, $y_j$.

In block 225, the regression model can be trained to identify candidate features for a feature vector set and predict the associated target properties.

After sufficiently training the regression model, the model can obtain candidate feature vectors set that can satisfy a user's query for selected properties with targeted values.

In block 230, the generated feature vectors in association with a target property selected from the different target properties available, can be compressed through one or more steps to a reduced dimension vector, for example, a two-dimensional vector, where the two-dimensional vectors of the known chemical compounds are represented in a two-dimensional feature space. The compressed feature vectors can be displayed on a map having at least two dimensions as icons at the coordinates of a relational vector on a graphical user interface (GUI).

In block 235, the relational vectors can be generated from the initial feature vectors of the feature vector set by a variational auto encoder (VAE), where the VAE reduces the dimension of the initial feature vector(s) through one or more compression steps that can reduce down to two-dimensions. Each compression step can be implemented as a separate hidden layer in a stochastic neural network (SNN), where the neural network is programmed and trained to form an intermediate reduced dimension vector at each compression step.

In a non-limiting exemplary embodiment, the initial feature vectors can be a plurality of 66×1 dimension feature vectors, where each is compressed to a 32×1 dimension intermediate vector by a hidden layer of a neural network, where the hidden layer has 32 nodes. The intermediate feature vectors can be further compressed to a reduced dimensional vector, for example, a 2×1 relational vector that can be mapped to a reduced dimension graph, for example, a two dimensional (2-D) graph, using additional hidden layers in the neural network, for example, a hidden layer with 8 nodes and a hidden layer with 2 nodes, to produce a 2×1 relational vector that is a compressed feature vector, z. The 2×1 relational vectors can be represented as the coordinates of a 2-D graph, where the 2-D graph is presented to a user on a display device.

In various embodiments, the 2×1 relational vector includes a value, σ, representing a dispersion value of a Gaussian distribution from which a compressed feature vector, z, is sampled.

In various embodiments, the 2×1 relational vector includes a value, μ, representing a mean value of a Gaussian distribution from which a compressed feature vector, z, is sampled.

Figure 3:
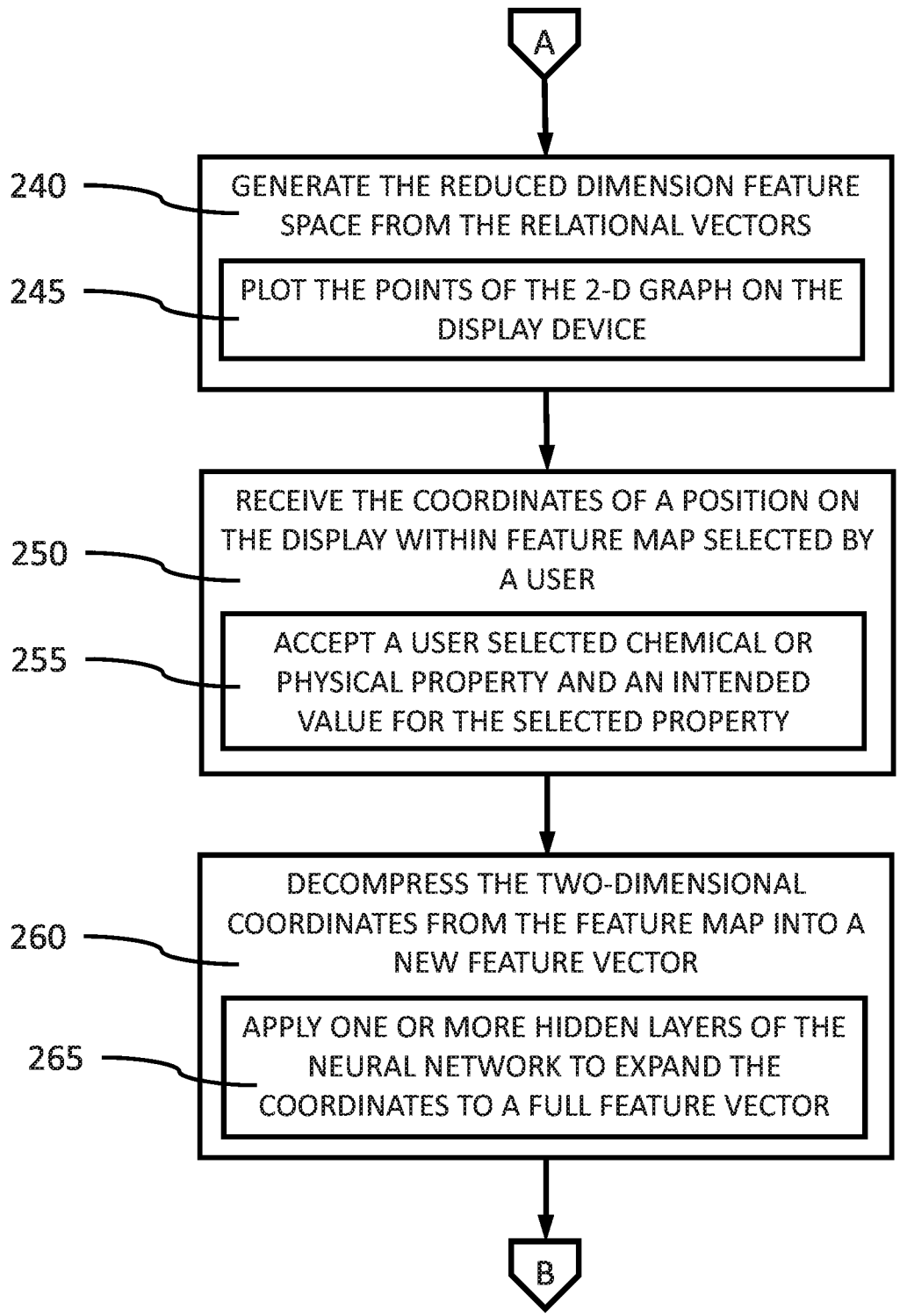
FIG. 3 is a continuation of the block/flow diagram of FIG. 2, in accordance with an embodiment of the present invention.

FIG. 3 is a continuation of the block/flow diagram of FIG. 2, in accordance with an embodiment of the present invention.

In block 240 the two-dimensional relational vectors can be represented in a two-dimensional (2-D) feature space by mapping the two dimensional point of each of the two-dimensional relational vectors generated from the known chemical compounds. The 2-dimension coordinates, however, are disconnected from the initial chemical structures by the compression of the feature vectors, so a user does not know exactly what chemical structures are represented by the points shown on the 2-D graph, but instead the relative relationship of the compressed feature vectors to the selected property. Areas on the display that lack known chemical compounds with the selected property having a desired value can appear as empty space(s). The two values, μ and σ, of each 2×1 relational vector can be plotted on a map having at least two dimensions presented on a display to a user.

In block 245, the map having at least two dimensions can be presented to a user on a display device (e.g., computer screen, monitor, etc.) graphically showing the relationship between the ingested chemical compounds and the associated property by a relative position to each other on the display device. The values of the 2×1 relational vector can be centered on the map and displayed as x and y coordinates representing the compressed feature vector, z=(σ, μ). In various embodiments, in which a variational auto encoder (VAE) is used for the compression process, the compressed feature vectors for the known chemical compounds are forced to be distributed around the origin (0, 0) with a Gaussian profile due to the nature of the VAE algorithm. In various embodiments in which VAE is not used, and a different compression algorithm is used, for example, principle component analysis (PCA), the plot of the compressed feature vector, z, can have a different plot on the display. In various embodiments, differences in the associated value of the selected property can be represented as different colors or shading of the icons displayed on the screen.

In block 250 a user can select a position on the vector space of the map by moving a cursor to a location on the displayed map and clicking on the location.

In one or more embodiments, the coordinates of the cursor position and the associated location on the map can be received (e.g., by the processing system) and used to identify the associate values (e.g., (σ, μ)) for a new relational vector (e.g., 2×1 vector) and associated property value (chemical or physical). The coordinates of the cursor position can have relative relationships with the plotted compressed feature vectors, z, based on displayed points nearness to the user selected position, where the further away a selected point is from the displayed points, the less similar a newly generated chemical structure will be from the chemical structures associated with the compressed feature vectors.

In block 255 a user can select a chemical or physical property that the user intends to use as a reference property for constructing a new chemical structure, for example, from a drop-down menu of the known properties (e.g., chemical, physical) for the original chemical compounds used to generate the initial feature vectors. The processing system can receive the selected chemical or physical property and use the property in the search algorithm, and to construct the new chemical structure. In various embodiments, one or more properties can be selected by the user. A sum-set of $x^{(j)}$ for all the selected properties $y_j$ can be utilized, where one or more chemical structure(s) that maximizes the sum of the two or more selected property values can be identified as the proposed new structure.

Physical properties can include, but not be limited to, melting point, freezing point, triple point, vapor pressure, heat capacity, refractive index, dielectric constant, resistivity, viscosity, glass transition temperature, thermal conductivity, coefficient of thermal expansion, elasticity/plasticity, and tensile strength. Physical properties can be measured independent of the desired chemical compound's environment or interaction with another material.

Chemical properties can include, but not be limited to, toxicity, standard enthalpy of formation, hydrophilicity/hydrophobicity, surface energy, pH, and dipole moment. Chemical properties can involve interactions between the desired chemical compound and another material.

In various embodiments, the user can input a desired value for each selected property, which can be received by the processing system, for use in the regression analysis and search algorithm. The inputted value can be a value different from the known values for the identified property associated with the known chemical compounds in the data set. The new set of values can be used to guide the development of a new compound having the new property values.

In a non-limiting exemplary embodiments, a user can select melting point as the physical property and surface energy as a chemical property for a new compound. The relational vectors for the known chemical compounds can be displayed with the selected property. A set of chemical structures with known substructures, known surface energy, and known melting points can be analyzed to determine the contributions (e.g., weighting coefficients) of each substructure to the properties. The contributions of the substructures can be determined through regression analysis and modeling by creating feature vectors for each of the chemical structures in the data set, where the different known melting points can be back-calculated in view of the substructures in each chemical compound. In various embodiments, a desired value for the properties (e.g., melting point and the surface energy) can be used as a filter in generating a new chemical structure. The inputted value for the new melting point can be used to identify and combine the various substructures to arrive at a new final structure having the desired value for the melting point. This can also be done for the surface energy, or a sum of the two values.

The regression model can be used to analyze the contribution of the different substructures and backbone and bonding arrangements to a particular chemical or physical property, and establish weighting coefficients for each of the chemical substructures (e.g., moieties). Information regarding the effect of the different substructures on a particular property can be used to identify substructure components for assembling a new chemical structure having a desired value for the property. The contributions of the substructures to the property value can be optimized to identify a particular chemical structure for synthesis and testing.

A regression model that uses an L1 regularization technique is called a Lasso Regression. Regularization is a process applied to objective functions of introducing additional information in order to prevent overfitting data points in arriving at a predicted function. $\lambda$ is a parameter which controls the importance of the regularization term. A regression model can automatically detect patterns in data, for example, the relationship between substructures in a chemical compound and a chemical or physical property, and then use the uncovered patterns to predict future outcomes. The L1 regularization can select effective substructures from a first set of chemical compounds.

A regression model that uses L2 regularization technique is called a Ridge Regression, where the difference between the L1 regression and the L2 regression is the form of the penalty term. L2 regularization can be applied to a second set of chemical compounds.

In one or more embodiments, the second portion of the process generates a new chemical structure from the analyzed structures by identifying the various substructures that contribute at least a portion to the identified property value. The weightings of different types of substructures to the property value can be used to design a chemical structure with the intended final value through a reverse process from the regression analysis. The new chemical structure is, thereby, designed by starting with desired chemical and/or physical properties and combining substructures that affect the desired chemical and/or physical properties to arrive at a final chemical structure. A search algorithm can be created to identify chemical substructures that contribute to an identified chemical or physical property. The weights can be used by the nodes of the neural network.

In block 260, the values of the point selected on a map having at least two dimensions can be used to construct a new chemical structure through decompression of a new relational vector (e.g., new 2×1 relational vector ($\sigma$, $\mu$)). The new relational vector can be input into additional hidden layers of the neural network, where the hidden layers perform an inverse operation on the values (e.g., ($\sigma$, $\mu$)) of the point selected on the map to generate decompressed feature vectors.

In block 265, the neural network constructs a new feature vector by reversing the layers applied to compress the initial features vectors. In various embodiments, there can be as many hidden layers performing decompression in the neural network as there were hidden layers performing compression of the initial feature vectors. The nodes of the hidden layers can include the weights initially used for compression of the feature vectors, where the weights of the one or more nodes in the hidden layers provide weighted association of the moieties identified for the new candidate feature vector of a new chemical compound.

Figure 4:
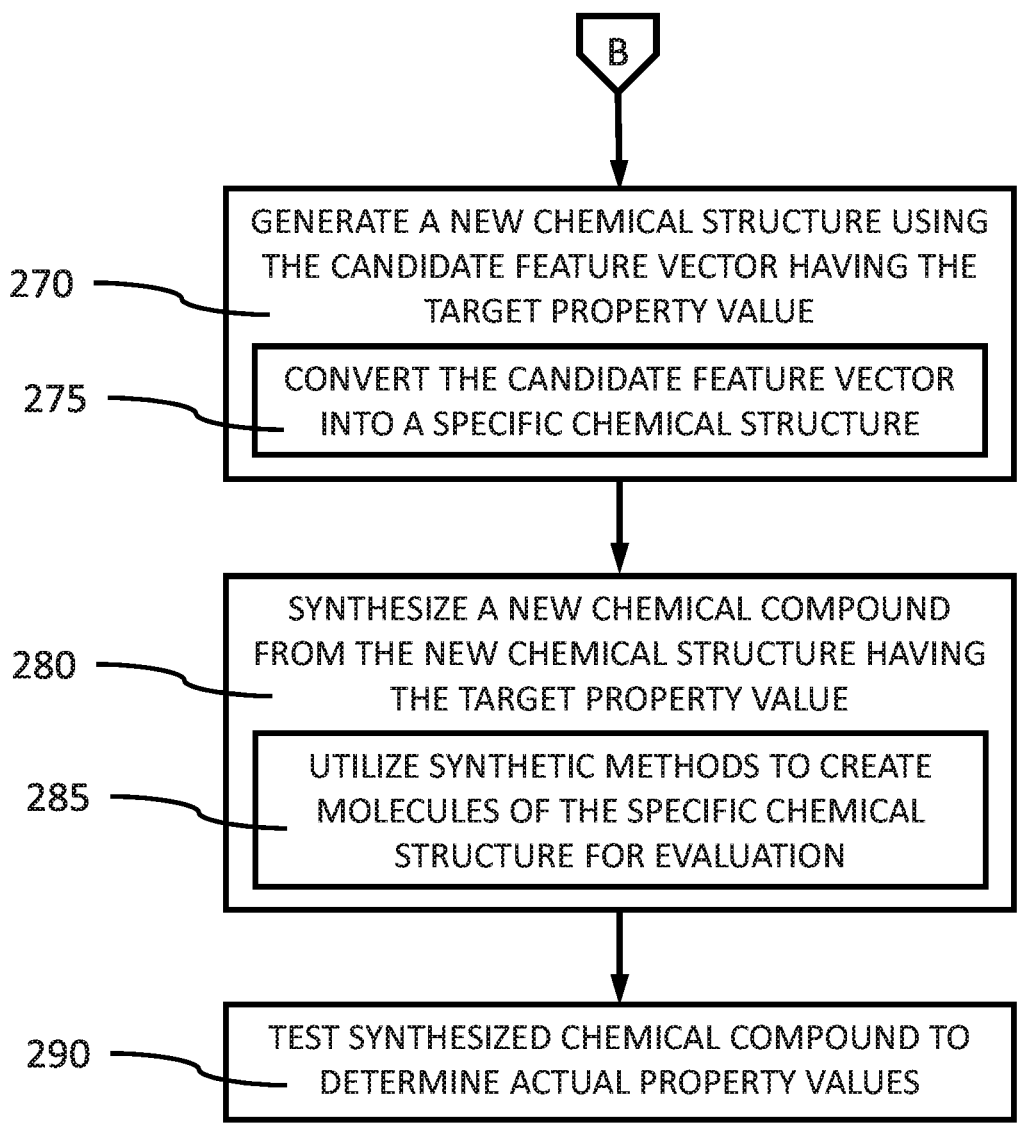
FIG. 4 is a continuation of the block/flow diagram of FIG. 3, in accordance with an embodiment of the present invention.

FIG. 4 is a continuation of the block/flow diagram of FIG. 3, in accordance with an embodiment of the present invention.

In block 270, a new chemical structure can be generated from the new reduced dimension relational vector having the property value closets to the desired value, as selected or input by the user.

In one or more embodiments, the decompression of the new reduced dimension relational vector produces a new candidate feature vector that identifies a set of structural features and moieties of a new chemical compound distinct from the chemical compounds represented by the initially digested feature vectors. The candidate feature vector can have the same dimensionality as the initial feature vectors, where the candidate feature vector is generated by the inverse hidden layers of the neural network. The candidate feature vector can be used to create a new chemical structure utilizing backbone structuring, atomistic detailing, and bonding detailing.

In various embodiments, backbone structuring can refer to the graph topology of a chemical structure without atomistic or bonding details in conformity with the rules of SMILES grammar. Graph nodes can be individual carbon atoms, C. Configurations and connections of rings (e.g., 5-membered and 6-membered) can be included, as well as linear and branched chains of carbons, C. Rings can be identified as bonded or fused. A possible connection sequence of the backbone structure can be generated from these components, where the arrangement can satisfy the requirement that a total number of atoms and a correct number of rings be represented. The connection sequence can be encoded in SMILES grammar.

In various embodiments, atomistic detailing can include specifying the correct number and arrangement of heteroatoms (i.e., atoms other than carbon and hydrogen), in and along the backbone structure.

In various embodiments, bonding detailing can include specifying the correct number and arrangement of chemical bonds other than single bonds (e.g., double bonds, triple bonds, and aromatic rings).

Actual chemical structures can be generated using the above process, but the number of possible structures increases exponentially (e.g., $10^1$-$10^2$) at each step due to the different available positions and connections of each new detail or modification, as represented by a position in a SMILES string.

In block 275, the candidate feature vector can be converted into a specific new chemical structure by identifying the number and arrangement of the chemical substructures output by the processing system from the search algorithm.

The generated candidate structures can be filtered at each step to eliminate candidate structures and/or substructures that have no or a negligible effect on a particular property. Each substructure can transform its own shape such that it becomes useful as a filter. The substructures can be modified to represent the actual substructures that can be assembled to form the new chemical compound. The substructures can initially be modified by generalizing all substructures to represent heteroatoms and chemical bonds as carbon atoms and single bonds for backbone structuring, since the additional atomistic and bonding details are not utilized at that step. The additional atomistic and bonding details can be reintroduced at the subsequent stages of the structure generation process. The atomistic details can be reintroduced by replacing the carbon atoms in the substructures remaining after the first round of filtering with the heteroatoms at their original positions in the substructures. A second stage of filtering can then be applied to the substructures containing the additional atomistic details to eliminate substructures that are not applicable. The bonding details can then be reintroduced to the substructures remaining after the second stage of filtering. The number of possible chemical structures can be suppressed by each stage of filtering. The candidate structures can be filtered using the counts of substructures appearing in $X_D^{Select}$.

In block 280, the new chemical compound can be synthesized from the new chemical structure having the target value for the chemical or physical property.

In block 285, the newly generated chemical structure can be synthesized using the various organic, inorganic, and/or polymer synthetic methods for testing and use. The new chemical structure can be used to prepare a synthetic pathway for making the new chemical compound.

In block 290 the synthesized chemical compound can be tested using various analytical and instrumental methods to determine the actual values for the selected chemical and/or physical properties. The testing can determine if the synthesized compound has the property values utilized in generating the candidate structure(s). Determination of the actual values of the chemical and/or physical properties can be fed back into the data set of known materials to fill in open spaces in the 2-D map.

Figure 5:
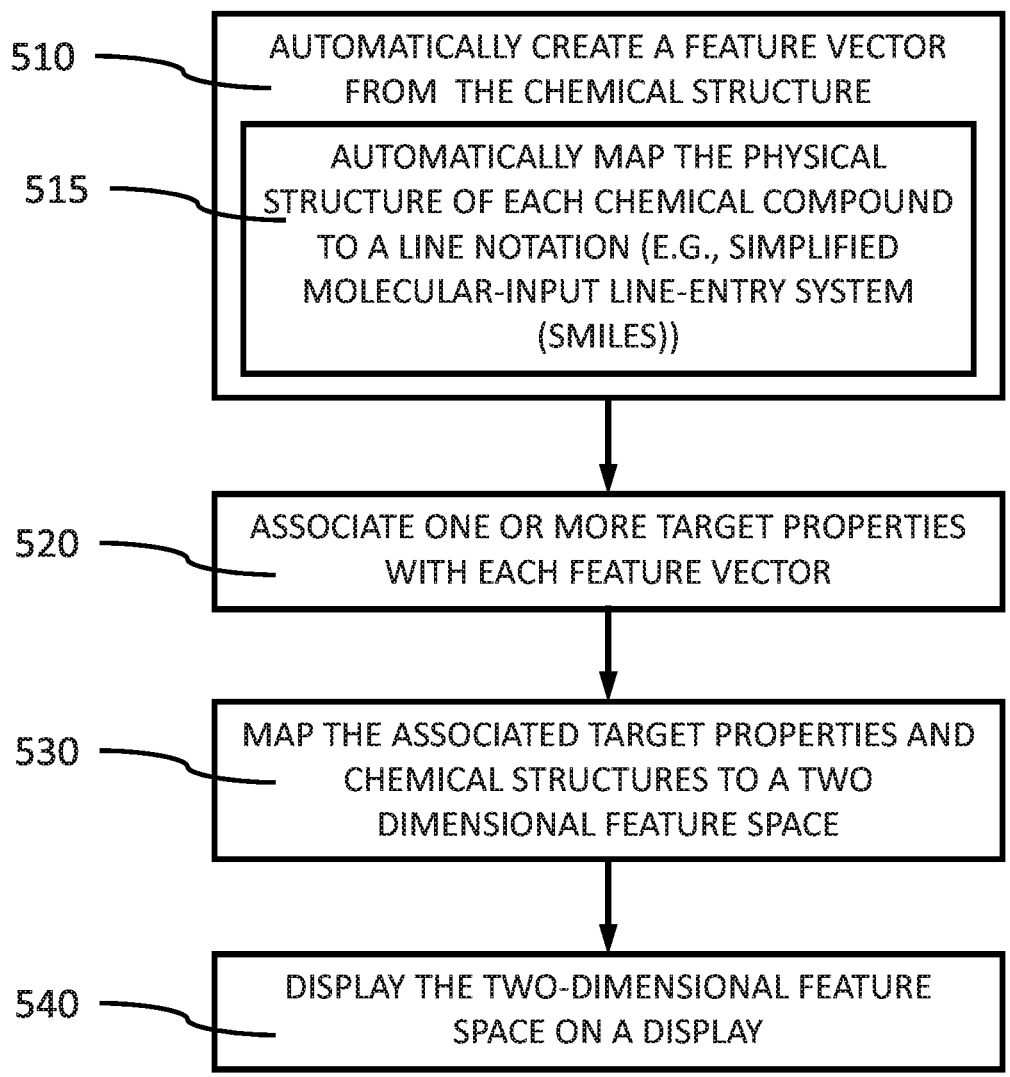
FIG. 5 is a block/flow diagram showing a method of creating a feature vector, in accordance with an embodiment of the present invention.

FIG. 5 is a block/flow diagram showing a method of creating a feature vector, in accordance with an embodiment of the present invention.

A feature vector can capture the known chemical compound's features in an accurate manner, where the feature vector can represent all of the possible chemical compound substructures without biasing the representation towards particular functional groups or backbone configurations.

In block 510, a representation of the chemical structures as feature vectors can be automatically generated using feature extraction based on known chemical bonding properties and identifiable functional groups without direct human input to define the substructures. The generated substructures for the feature vector can be recognized by users as functional groups and backbone structures utilized in the chemical arts to describe and synthesize new compounds. The substructures for the feature vector can also be recognized by users as features that affect known physical and chemical properties.

The feature vectors can be of two different types. A first type of feature vector can include substructure counts that determines and records the number of each substructure identified in each chemical compound through the automatic process from the data set of chemical compounds. The automatically generated set of substructures and counts can include segments of a chemical compound that do not correspond to a readily identifiable functional group or backbone structure.

A second type of feature vector can include substructure counts that determines and records the number of each substructure identified as a known functional group or backbone structure in the chemical compound, such that the substructures can potentially generate new structures that are more easily identifiable and synthesizable by a user.

In block 515, for the first type of feature model, let $M=\{m_1, m_2, m_3, \ldots, m_{n-1}, m_n\}$, where M is a set of the chemical compounds, $m_i$, where i is an index=1 to n, and n is the total number of molecules included in the data set of chemical compounds. The structure and substructures of a chemical compound, $m_i$, can be analyzed to automatically identify sets of substructures for each chemical compound.

Let $S_m=\{s_{i,1}, s_{i,2}, s_{i,3}, \ldots, s_{i,k}\}$, where $S_m$ is a set of elements, $s_{i,j}$, where i is the index of the chemical compound, and j is an index=1 to k for the substructures of the identified compound, $m_i$. $S_{1,j}$, can be the set $\{s_{1,1}, s_{1,2}, s_{1,3}, \ldots, s_{1,n}\}$ of the actual substructures of chemical compound 1. In various embodiments, $S_m$ can be an exhaustive set, $S^{full}$, such that $S_m$ includes all possible substructure representations for a chemical compound, $m_i$, from the individual atoms up to the entire molecule. The substructures can be identified using rules that identify all the possible permutations of atoms and bonds between the atoms for a chemical compound. In various embodiments, a Morgan Fingerprint approach can be used in preparing data-driven feature vectors for a set of chemical structures using an exhaustive analysis.

An exhaustive (i.e., complete) set, $S^{full}$ of substructures can be created for the set of chemical compounds, M, in the data set, where $S^{full} = \cup_{i=1}^{N} S^{(i)}$, where N denotes the number of chemical compounds.

In one or more embodiments, an exhaustive set, $S^{full}$, for an entire set, M, of molecules, can be represented as $S^{full} = \cup_i S^{(i)}$, for i=1 to N. In other words, by expanding the elements of $S^{full}$ to be $S_1^{full}, S_2^{full}, S_3^{full}, \ldots$ a vector for the chemical compound, $m_i$, can be represented as $X_D^{(n)} := (N_D(m_i, S_1^{full}), (N_D(m_i, S_2^{full}), (N_D(m_i, S_3^{full}), \ldots)$. $X_D^{(n)}$ represents the topological feature of a molecular structure by incorporating the counts of all partial graphs appearing in $m_i$. Due to the exhaustiveness, the information in $X_D^{(n)}$ includes substantial redundancy. For example, most of the substructures in $S^{full}$ may appear only once or a few times even in the full molecules set M; therefore, using them all is not suitable.

Let $N_D = \{n_{i,1}, n_{i,2}, n_{i,3}, \ldots, n_{i,j}\}$, where $n_{i,j}$ is the quantity of each identified substructure, $s_{i,j}$, of a first chemical compound $m_i$.

A molecular structure and a substructure can be represented as graphs composed of nodes (atoms) and edges (chemical bonds), $S_m = \{s_{i,1}, s_{i,2}, s_{i,3}, \ldots, s_{i,k}\}$ can form a partial graph of m.

To select only the substructures that affect the target property, a feature selection process can be performed on it. By denoting the target property as t, a LASSO (Least Absolute Shrinkage and Selection Operator) regression model $\mathcal{L}: x_D \mapsto y$ can be created. Tuning the hyperparameter (degree of $L_1$ penalty term) and setting a threshold $w_{th}$ for absolute value of regression coefficient |w|, the system selects important substructures. We denote the set of selected substructures as $S^{Select}$, and corresponding feature vector as $X_D^{Select}$. $X_D^{Select}$ can be referred to as a data-driven substructure feature set. The substructure selection can be accomplished by L1 regularization to select effective substructures. L2 regularization can be utilized for substructure selection for the predefined components of the predefined component set.

A final structure set can be a concatenation of a data-driven substructure feature set and a predefined component feature set, $x:=(X_D^{Select}, x_P)$.

There may be exceptions for target properties that are low level (i.e., atomistic level properties such as energy bandgap etc.), not mesoscopic molecular level or macroscopic functional level (e.g., luminescent efficiency), so that the properties of the myriad number of chemical compounds can be calculated by physical simulation (e.g., DFT simulation).

In block 520, one or more target properties can be associated with each feature vector.

In block 530, the associated target properties and chemical structures can be mapped to a two dimensional feature space.

In block 540, the two dimensional feature space can be displayed on a display device.

In one or more embodiments, the predicted chemical structure can be synthesized to provide a physical organic molecule, inorganic compound, polymer, or other chemical for testing and review of the resulting properties. The organic molecule(s) may be synthesized using known organic preparatory methods available to chemists. Polymers may be prepared by synthesizing the organic monomer using known organic preparatory methods and polymerizing the resulting monomer to produce the polymer. Inorganic compounds may be synthesized using known inorganic preparatory methods.

In various embodiments, the resulting chemical compound can be tested to determine if the compound has the desired value for the intended physical or chemical property.

FIG. 6 is a diagram showing a set of predefined features used to form a predefined component feature vector, in accordance with an embodiment of the present invention.

In one or more embodiments, backbone components of the predefined feature vector can include, for example, substructures: (A) bonded 5-member rings, (B) fused 5-member rings, (C) bonded 6-member rings, (D) fused 6-member rings, (E) linear bonded carbon chains, (F) branched bonded carbons, (G) ether bond, and (H) alcohol groups.

Figure 7:
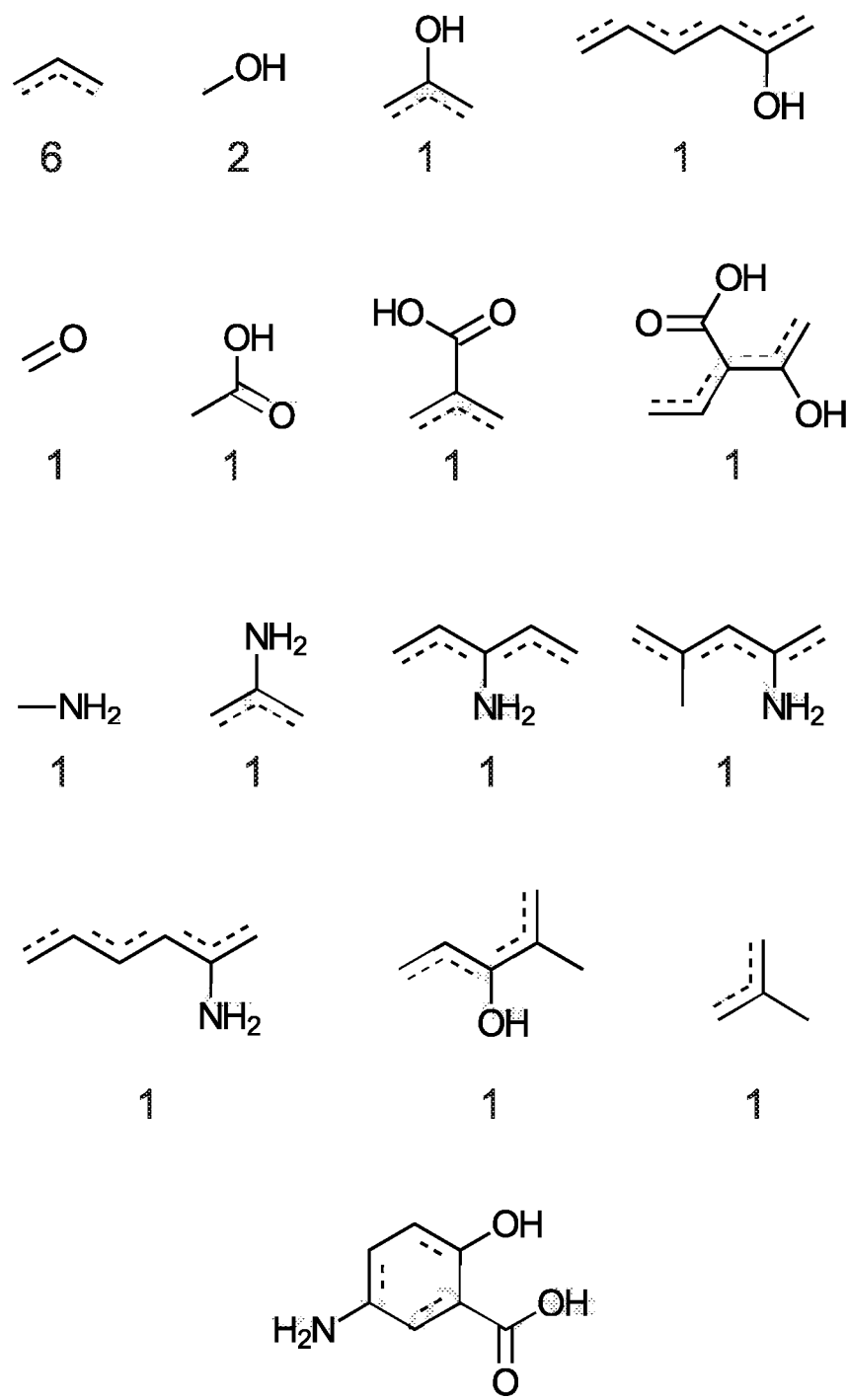
FIG. 7 is a diagram showing a set of possible substructures generated from a known chemical compound for a data-driven feature set, in accordance with an embodiment of the present invention.

FIG. 7 is a diagram showing a set of possible substructures generated from a known chemical compound for a data-driven feature set, in accordance with an embodiment of the present invention.

Each substructure including from 1 to 11 atoms in the original structure can be identified by examining all possible combinations of adjoining atoms making up the chemical compound, and transforming cyclic components into linear or branching arrangements. The number of each substructure identified in the original compound is presented below the substructure. The substructures can form a data-driven substructure set, and the counts can form a data-driven substructure feature vector.

Figure 8:
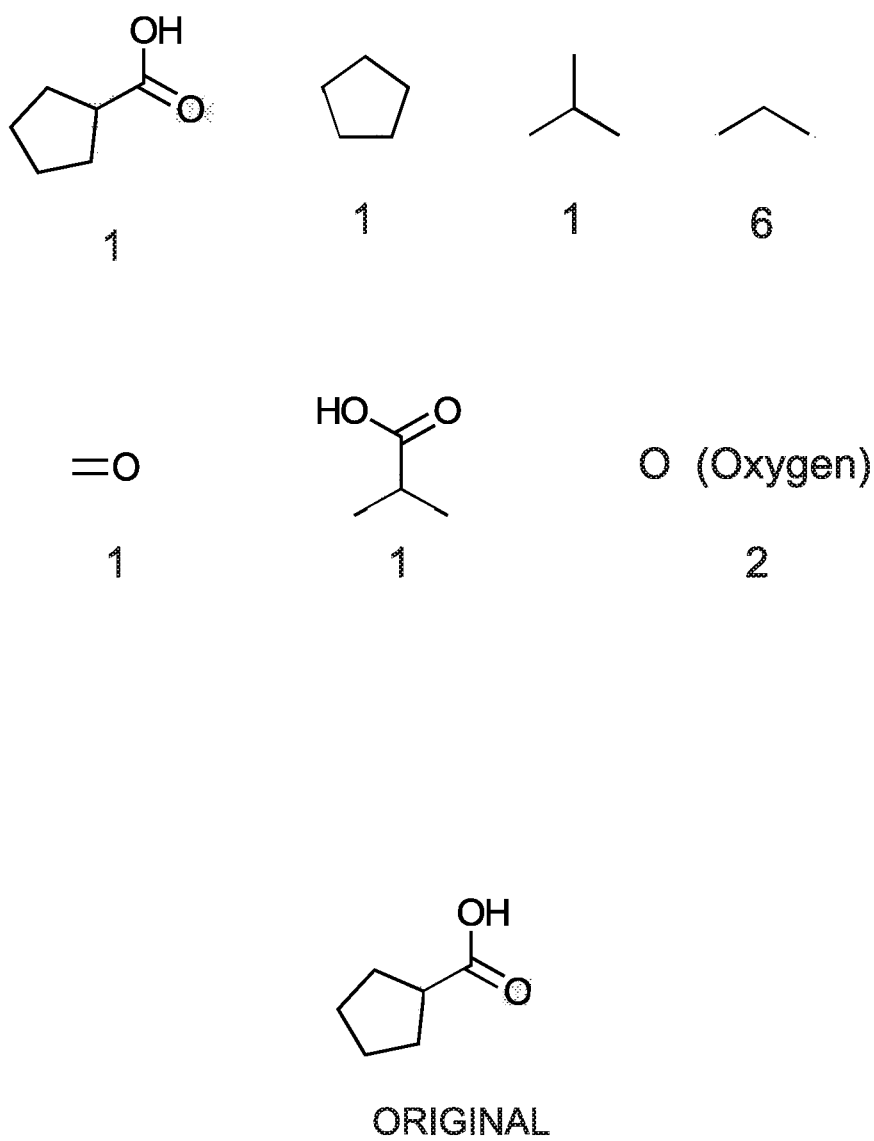
FIG. 8 is a diagram showing a set of possible substructures generated from a known chemical compound for a predetermined feature set, in accordance with an embodiment of the present invention.

FIG. 8 is a diagram showing a set of possible substructures generated from a known chemical compound for a predetermined feature set, in accordance with an embodiment of the present invention.

Utilizing recognized representations of the molecular components from which the original compound can be constructed, a predefined component set and predefined component feature vector can be constructed.

Figure 9:
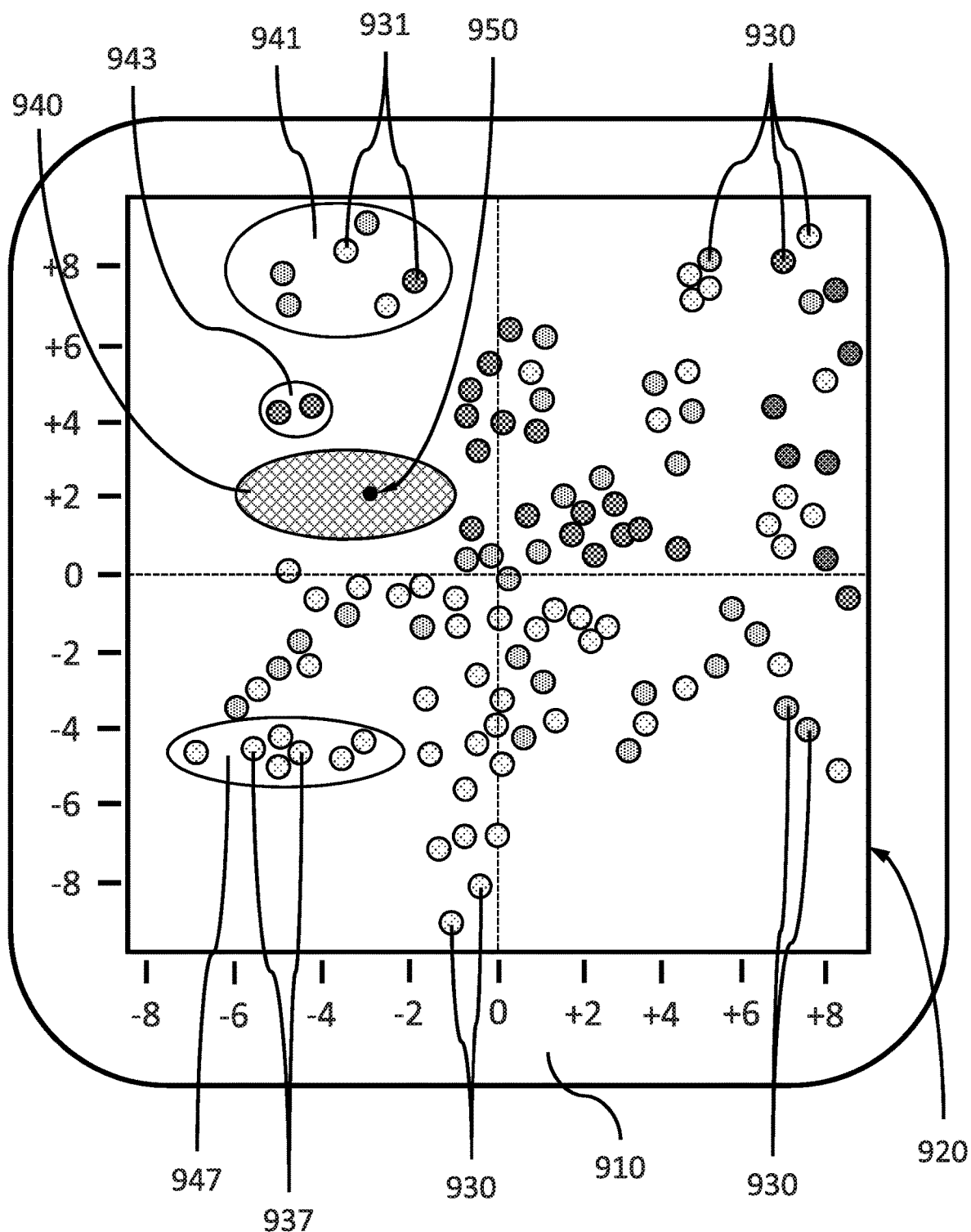
FIG. 9 is a map presented on a display, in accordance with an embodiment of the present invention.

FIG. 9 is a two dimensional map presented on a display, in accordance with an embodiment of the present invention.

In one or more embodiments, a plurality of icons 930, 931, 937 can be shown on a two dimensional map 920 being displayed on a display device 910. The icons 930, 931, 937 can be dots located on the 2 dimensional map 920 according to the values of each of the 2×1 relational vectors. The icons can be clustered around the origin 0, 0, and show a dispersal depending on how the two-dimensional vectors were generated from the initial feature vectors of the feature vector set. In various embodiments, the 2×1 dimensional relational vectors can each be displayed on the display device, as icons 930, 931, 937 having different colors or shading representing relative differences in the associated value of the selected chemical or physical property. The colors or shading can indicate the value of the selected chemical or physical property of the related chemical structure in comparison to the values of the other plotted chemical structures.

In one or more embodiments, a user can identify a position 950 on the 2-D map 920 by placing a cursor at the desired location, where the size and shape of the cursor can be chosen by the user. The position 950 of the cursor can be within an empty space 940 of the 2-D mapping. The position 950 of the cursor can identify a new pair of values for a 2×1 relational vector, where the values can uniquely correspond to a new chemical compound structure.

In various embodiments, the icons 931, 937 can be clustered in particular areas of the 2-D map 920 at positions in the vicinity of the position 950, where a newly generated chemical structure can have the closest similarity to chemical structures represented by the icons in cluster 943. The chemical structures represented by the icons 931 in cluster 941 can be somewhat similar to a newly generated chemical structure due to the increased relative distance compared to the icons in cluster 943. The chemical structures represented by the icons 937 in cluster 947 can be dissimilar to a newly generated chemical structure due to the even greater relative distance of position 950 from icons 937 in cluster 947 and the intervening icons between the cluster 947 and position 950.

In various embodiments, the coordinates of position 950 can be communicated to a processing system to generate one or more new feature vector(s) for a new chemical compound using a stochastic neural network.

Figure 10:
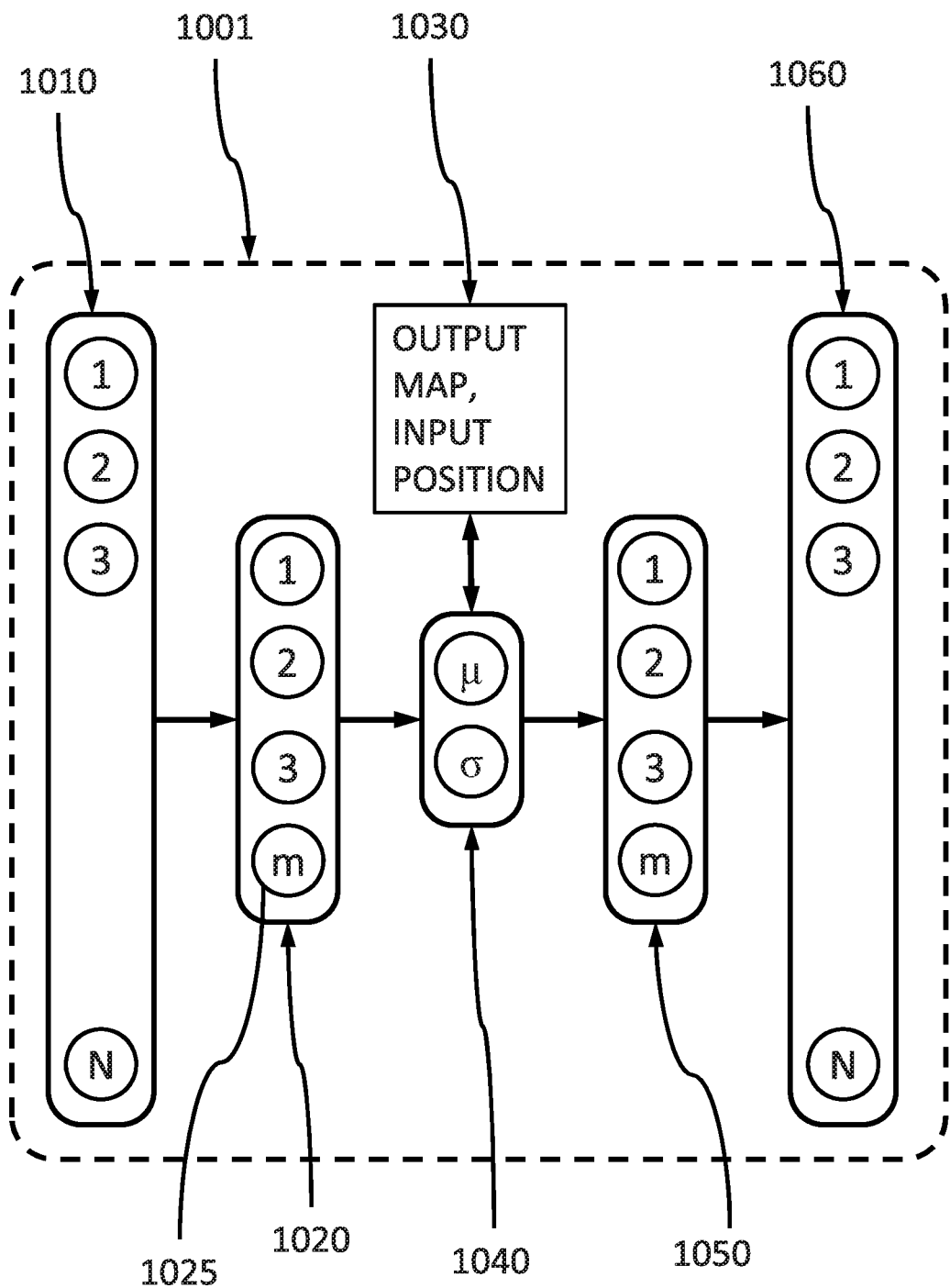
FIG. 10 is a block diagram of the layers of a stochastic neural network performing compression of feature vectors and decompression of a new 2×1 relational vector, in accordance with an embodiment of the present invention.

FIG. 10 is a block diagram of the layers of a stochastic neural network performing compression of feature vectors and decompression of a new 2×1 relational vector, in accordance with an embodiment of the present invention.

In one or more embodiments, one or more feature vector(s) 1010 having an N×1 dimension, can be input into a stochastic neural network (SNN) 1001 operating on a computer system 100. The SNN 1001 can compress each inputted feature vector 1010 down to a 2×1 relational vector 1040 using one or more hidden layers 1020 including a number, m, of nodes 1025, where the number, m, of nodes can be the reduced dimension of an intermediate vector.

In various embodiments, the 2×1 relational vectors 1040 are output as a mapping to a display device, and input of a position on the mapping generates a new 2×1 relational vector 1040. The new 2×1 relational vector can be decompressed using hidden layer(s) 1050 to generate a new feature vector 1060 also having an N×1 dimension.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer implemented method of generating new chemical compounds, comprising:
preparing a feature vector for each of a plurality of chemical compounds for which a chemical or physical property is known;
compressing each of the feature vectors into a relational vector;
mapping each of the relational vectors to a map having at least 2 dimensions;
presenting the map to a user on a display device;
receiving a selection of a position on the map from the user, wherein the position is converted to a new relational vector, wherein the new relational vector includes a coordinate value, $\alpha$, representing a dispersion value of a Gaussian distribution from which a compressed feature vector, z, is sampled, and a value, $\mu$, representing a mean value of a Gaussian distribution from which the compressed feature vector, z, is sampled;
decompressing the new relational vector to a candidate feature vector; and
generating a new chemical structure from the candidate feature vector.

2. The computer implemented method of claim 1, wherein each of the feature vectors is compressed into a 2-dimensional relational vector by one or more hidden layers of a neural network.

3. The computer implemented method of claim 2, wherein the neural network is a stochastic neural network.

4. The computer implemented method of claim 1, further comprising synthesizing the new chemical structure.

5. The computer implemented method of claim 1, wherein selection of a chemical and/or physical property is also received from the user.

6. The computer implemented method of claim 5, wherein the data-driven substructure feature vector uses SMILES grammar to represent the plurality of chemical compounds, and the predefined component feature vector uses SMILES grammar to represent the predefined chemical substructures.

7. The computer implemented method of claim 6, further comprising testing the synthesized candidate structure to determine the actual value for the chemical or physical property.

8. A system for generating new chemical compounds, comprising:
a display device;
memory, wherein a data set of a plurality of chemical compounds for which a chemical or physical property is stored in the memory;
a processor device, wherein the processor device is configured to prepare a feature vector for each of a plurality of chemical compounds for which a chemical or physical property is known;
a chemical structure generator configured to compress each of the feature vectors into a relational vector;
map each of the relational vectors to a map having at least two dimensions;
present the map to a user on the display device;
receive a selection of a position on the map from the user, wherein the position is converted to a new relational vector, wherein the new relational vector includes a coordinate value, $\sigma$, representing a dispersion value of a Gaussian distribution from which a compressed feature vector, z, is sampled, and a value, $\mu$, representing a mean value of a Gaussian distribution from which the compressed feature vector, z, is sampled;
decompress the new relational vector to a candidate feature vector; and
generate a new chemical structure from the candidate feature vector.

9. The system of claim 8, wherein each of the feature vectors is compressed into the relational vector by one or more hidden layers of a neural network.

10. The system of claim 9, wherein the neural network is a stochastic neural network.

11. The system of claim 10, wherein selection of a chemical and/or physical property is also received from the user.

12. The system of claim 11, wherein the data-driven substructure feature vector uses SMILES grammar to represent the plurality of chemical compounds, and the predefined component feature vector uses SMILES grammar to represent the predefined chemical substructures.

13. The system of claim 12, wherein the candidate structure is generated using backbone structuring, atomistic detailing, and bond detailing.

14. A non-transitory computer readable storage medium comprising a computer readable program for generating new chemical compounds, wherein the computer readable program when executed on a computer causes the computer to perform the steps of:
preparing a feature vector for each of a plurality of chemical compounds for which a chemical or physical property is known;
compressing each of the feature vectors into a relational vector;
mapping each of the relational vectors to a map having at least two dimensions;
presenting the map to a user on a display device;
receiving a selection of a position on the map from the user, wherein the position is converted to a new relational vector, wherein the new relational vector includes a coordinate value, σ, representing a dispersion value of a Gaussian distribution from which a compressed feature vector, z, is sampled, and a value, μ, representing a mean value of a Gaussian distribution from which the compressed feature vector, z, is sampled;

decompressing the new relational vector to a candidate feature vector; and generating a new chemical structure from the candidate feature vector.

15. The computer readable storage medium of claim 14, wherein each of the feature vectors is compressed into the relational vector by one or more hidden layers of a neural network.

16. The computer readable storage medium of claim 15, wherein the neural network is a stochastic neural network.

17. The computer readable storage medium of claim 14, wherein selection of a chemical and/or physical property is also received from the user.

18. The computer readable storage medium of claim 14, further comprising instructions for synthesizing the new chemical structure.

\* \* \* \* \*